(12) United States Patent
Arena et al.

(10) Patent No.: US 8,271,401 B2
(45) Date of Patent: Sep. 18, 2012

(54) EXPERT SYSTEMS AS A METHOD OF DELIVERING DIAGNOSTIC, PROBLEM SOLVING, AND TRAINING TECHNICAL SERVICES TO CUSTOMERS

(75) Inventors: Blaise J. Arena, Des Plaines, IL (US); Veronica M. May, Des Plaines, IL (US); Alan Zagoria, Des Plaines, IL (US); Martha S. Buchan, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 1037 days.

(21) Appl. No.: 12/118,976

(22) Filed: May 12, 2008

(65) Prior Publication Data

US 2009/0030856 A1   Jan. 29, 2009

Related U.S. Application Data

(60) Provisional application No. 60/961,731, filed on Jul. 24, 2007.

(51) Int. Cl.
G06F 17/00 (2006.01)
G06F 17/20 (2006.01)
(52) U.S. Cl. ........................................................ 706/11
(58) Field of Classification Search .................. None
See application file for complete search history.

(56) References Cited

U.S. PATENT DOCUMENTS

| 4,763,277 A | 8/1988 | Ashford et al. ............... 364/513 |
| 5,274,801 A | 12/1993 | Gordon et al. ................ 395/600 |
| 5,301,314 A * | 4/1994 | Gifford et al. ........................ 1/1 |
| 6,009,420 A | 12/1999 | Fagg, III et al. ................. 706/45 |
| 6,012,051 A | 1/2000 | Sammon, Jr. et al. .......... 706/52 |
| 6,243,090 B1 | 6/2001 | Machiraju et al. ............ 345/338 |
| 6,560,590 B1 | 5/2003 | Shwe et al. ...................... 706/55 |
| 6,728,692 B1 | 4/2004 | Martinka et al. ................ 706/45 |

(Continued)

FOREIGN PATENT DOCUMENTS

KR         2015887 A       3/2002

(Continued)

OTHER PUBLICATIONS

Foo, Schubert et al.; "A Web-based Intelligent Help Desk Support Environment"; 2002; International Journal of Systems Science, 33(6); pp. 1-20.*

(Continued)

Primary Examiner — Jeffrey A Gaffin
Assistant Examiner — Stanley K Hill
(74) Attorney, Agent, or Firm — Maryann Maas

(57) ABSTRACT

An expert system may be utilized for providing and receiving interactive, computer-implemented support services related to chemical processing units. The expert system may include a knowledge base that contains information coded in the form of rules, decision trees, and logic and a database that stores and handles various types of information related to the expert system. A query component receives a query that may be a problem, a performance issue, or a training request selected from a list or diagram or otherwise generated by a customer. An answer component utilizes the knowledge base, the database, an external database, and/or an expert to provide one or more answers to the query. A question and answer session may be initiated by the expert system in order to gain further information and detail related to the query. Supplemental information and the identified answers may be provided to the customer.

18 Claims, 10 Drawing Sheets

U.S. PATENT DOCUMENTS

| | | | |
|---|---|---|---|
| 6,763,342 B1 | 7/2004 | Mattern et al. | 706/46 |
| 6,850,923 B1 | 2/2005 | Nakisa et al. | 706/47 |
| 6,901,394 B2 | 5/2005 | Chauhan et al. | 706/60 |
| 7,007,245 B2 | 2/2006 | D'Souza et al. | 715/853 |
| 7,146,535 B2 * | 12/2006 | Little et al. | 714/26 |
| 2002/0099679 A1 | 7/2002 | Usitalo et al. | 706/46 |
| 2002/0103777 A1 | 8/2002 | Zhang | 706/59 |
| 2002/0138786 A1 * | 9/2002 | Chefalas et al. | 714/37 |
| 2003/0004795 A1 | 1/2003 | Monrad | 705/14 |
| 2003/0004909 A1 | 1/2003 | Chauhan et al. | 706/45 |
| 2004/0024724 A1 | 2/2004 | Rubin | 706/55 |
| 2005/0010544 A1 | 1/2005 | Sleat | 706/46 |
| 2005/0097067 A1 | 5/2005 | Kirshenbaum | 706/46 |
| 2005/0161260 A1 * | 7/2005 | Koithan et al. | 175/57 |
| 2006/0112055 A1 | 5/2006 | Tapio et al. | 706/46 |
| 2006/0200371 A1 | 9/2006 | Spector et al. | 705/7 |

FOREIGN PATENT DOCUMENTS

| | | |
|---|---|---|
| KR | 0446640 B1 | 9/2004 |
| WO | WO 2005059777 A1 * | 6/2005 |

OTHER PUBLICATIONS

Hui, S.C. et al.; "A web-based intelligent fault diagnosis system for customer service support"; 2002; Elsevier Science Ltd.; Engineering Applications of Artificial Intelligence 14; pp. 537-548.*

Chan, Christine W. et al.; "Knowledge engineering for an intelligent case-based system for help desk operations"; 2000; Elsevier Science Ltd.; Expert Systems with Applications 18; pp. 125-132.*

Hui, S.C. et al.; "Data mining for customer service support"; 2000; Elsevier Science; Information & Management 38; pp. 1-13.*

Nong Ye; "Self-adapting decision support for interactive fault diagnosis of manufacturing systems"; 1996; Taylor & Francis Ltd; Int. J. Computer Integrated Manufacturing, vol. 9, No. 5; pp. 392-401.*

Baartman, Jan P. et al.; "Placing Surface Mount Components Using Coarse/Fine Positioning and Vision"; 1990; IEEE; IEEE Transactions on Components, Hybrids, and Manufacturing Technology, vol. 13, No. 3; pp. 559-564.*

Mo, John P. T. et al.; "An integrated process model driven knewledge based system for remote customer support"; 1998; Elsevier; Computers in Industry 37; pp. 171-183.*

Foo, Schubert et al.; "An integrated help desk support for customer services over the World Wide Web—a case study"; 2000; Elsevier; Computers in Industry 41; pp. 129-145.*

Hui, S. C. et al.; "A web-based intelligent fault diagnosis system for customer service support"; 2001; Elsevier; Engineering Applications of Artificial Intelligence 14; pp. 537-548.*

PCT International Search Report and Written Opinion for PCT/US2008/070639 dated Feb. 17, 2009; 6 pages.

Ioannis M. Dokas, *Developing Web Sites for Web Based Expert Systems: A Web Engineering Approach*, Nov. 2002, pp. 1-15.

* cited by examiner

EXPERT SYSTEMS AS A METHOD OF DELIVERING DIAGNOSTIC, PROBLEM SOLVING, AND TRAINING TECHNICAL SERVICES TO CUSTOMERS

CROSS-REFERENCE TO RELATED APPLICATION

This application claims priority from Provisional Application Ser. No. 60/961,731 filed Jul. 24, 2007, the contents of which are hereby incorporated by reference.

TECHNICAL FIELD

This disclosure relates to expert systems and methods of delivering services to customers.

BACKGROUND

Customers of various technologies often require assistance in utilizing the technologies or in utilizing products that employ the technologies. A customer may encounter a problem that, if not solved, will result in losses to their business or will create some other adverse effect. Or the customer may desire additional training and/or supplemental information related to the technology. Thus, experts of the technology may often be heavily relied upon to assist in solving the problem or to provide the training and/or supplemental information. The experts' assistance may be needed globally and instantly. Additionally, the experts' assistance should include a systematic and efficient approach. Such assistance is traditionally done through phone conversations, on-site visits, and/or, more recently, email exchanges. Multiple conversations, visits, and/or exchanges may often be necessary, making the assistance a timely and inconvenient process. Moreover, an expert may not be readily available. The customer may not have the ability to timely supply important information that is critical to the problem. Also, the customer may struggle to accurately represent the problem to the expert.

Expert systems are computer programs that are used in various technologies, such as in the medical, financial, and manufacturing fields, to provide multiple types of expert assistance to a customer. An expert system is meant to supplement an expert in a particular technology by mimicking an interaction between the expert and a customer. An expert system further improves access to the experience of the expert and to knowledge related to a technology.

However, current expert systems lack in several areas. For example, expert systems exist for specific mass-produced products but are not available for customized units that are part of dynamic systems in which the components of the system are inter-dependent upon one another. In fact, the use of expert systems by customers and operators of such customized units is not currently employed.

SUMMARY

A delivery of support services related to one or more units includes the use of an interactive, computer-implemented expert system. Each unit may be an inter-dependent and dynamic unit that interacts with one or more supplemental units. The expert system may communicate with customers of the units over a network and may be a web-based application. The expert system may include a knowledge base that contains information coded in the form of rules, decision trees, and logic and a database that stores and handles various types of information related to the expert system. A query component receives a query that may be a problem, a performance issue, or a training request that is selected from a list or diagram provided by the expert system or otherwise generated by a customer. An answer component utilizes the knowledge base, the database, an external database, and/or an expert to provide one or more answers to the query. A question and answer session may be initiated by the expert system to gain further information or more detail related to the query. An interactive decision tree, which is a graphical representation of at least a portion of a knowledge base related to the unit or units and which includes branches containing multiple answers to each question related to the query, may be utilized by the system to identify answers to the query. The decision tree may be provided to the customer. Supplemental information related to the query and/or units, in addition to the answers to the query, may also be provided to the customer during a session with the expert system.

A delivery of support services related to one or more units may include a provision of interactive, computer-implemented support services to the customer during a portion of a lifespan of the one or more units. A query from a requester may be received and may be related to one or more aspects with the one or more units. Possible answers to the query may be identified and provided to the requester. The support services may be adapted to be applied to any of the units, and the units may be custom-designed.

A unit may be designed to meet selected criteria of a customer and interactive, computer-implemented support services may be provided to the customer to enable the customer to provide one or more products from a unit. The unit may include inter-dependent and dynamic components and may interact with supplemental units. The interactive, computer-implemented support services may include receiving a query related to an aspect of the unit and/or supplemental units, identifying one or more possible answers, and providing the identified answers.

A customer may utilize an interactive, computer-implemented support service by generating a query related to an aspect of one or more units during a portion of a lifespan of the one or more units. The query may be provided to the support service, and answers to the query may be received by the customer.

BRIEF DESCRIPTION OF THE DRAWINGS

The foregoing Summary and the following Detailed Description are better understood when read in conjunction with the appended drawings. Exemplary aspects are shown in the drawings; however, it is understood that the aspects are not limited to the specific methods and instrumentalities depicted herein. In the drawings.

DETAILED DESCRIPTION

Figure 1:
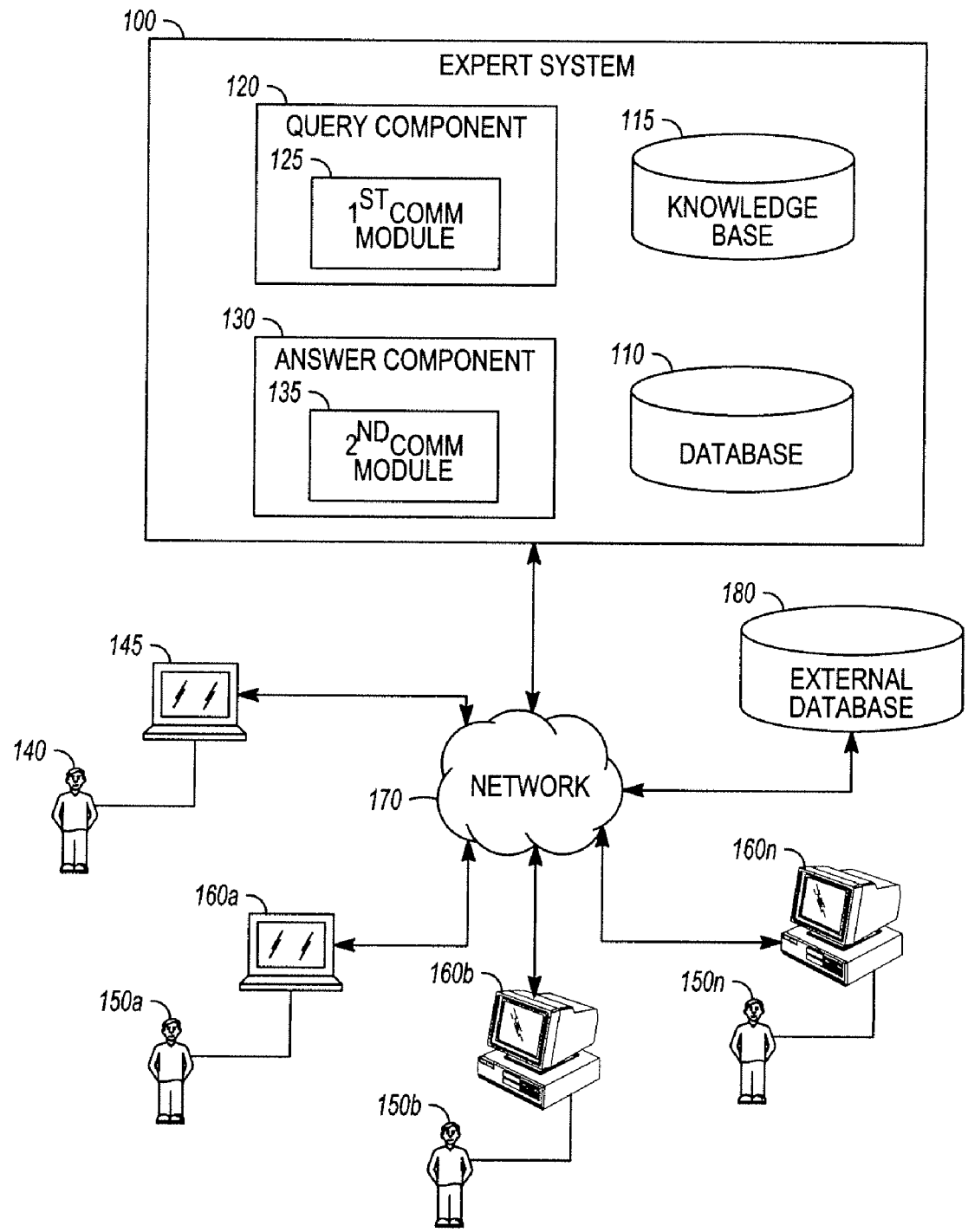
FIG. 1 is a block diagram illustrating an exemplary expert system for providing and receiving interactive, computer-implemented support services.

With reference to FIG. 1, an exemplary expert system 100 is illustrated. The exemplary expert system 100 may be utilized for providing and receiving interactive, computer-implemented support services. The expert system 100 may include a database 110, a knowledge base 115, a query component 120, and an answer component 130.

The database 110 may be a persistent, relational database that stores and handles various types of information. The knowledge base 115 may contain information coded in the form of rules, decision trees, and logic. The database 110 and knowledge base 115 may communicate with the components 120 and 130 of the expert system 100. For example, the database 110 and knowledge base 115 may receive from the query component 120. Similarly, the database 110 and knowledge base 115 may transmit information to the answer component 130. The database 110 may accordingly store information from the query component 120. The database 110 may organize the information according to pre-defined parameters. For example, the database 110 may automatically delete information that has not been accessed during a pre-defined period of time. The information stored in the database 110 may be assigned an identifier according to, for example, the type, length, or frequency of use of the information. Or an administrator 140 or a requester 150a-150n of the system may provide the identifier. The pre-defined parameters may be established by the administrator 140 of the expert system 100.

Various requesters 150a-150n may communicate with the expert system 100 with devices 160a-160n over a network 170. Three requesters, 150a, 150b, and 150n, are shown with three devices, 160a, 160b, and 160n, although more or fewer requesters 150 and devices 160 may be used with the expert system 100. Each requester 150 may utilize more than one device 160. The administrator 140 may utilize an administrator device 145. The network 170 may be a wide area network, a local area network, a public switched telephone network, or any other network or means capable of communicating between the system 100 and the devices 145 and 160a-160n. The devices 145 and 160 may be a device capable of communicating over the network 170 and processing the communications, such as a desktop computer or a laptop computer. The devices 145 and 160 may include a display, such as a monitor, for viewing the communications with the expert system 100.

A customer may operate one or more units, such as chemical processing units, such as those found in petroleum refineries, gas processing facilities, or petrochemical facilities. During at least a part of a lifespan of the one or more units, the customer may require expert assistance related to the one or more units or portions of the units or subunits thereof. The expert assistance may be related to a problem the customer is experiencing with the one or more units. Alternatively or additionally, the customer may desire expert assistance for a performance issue and/or for additional training related to the one or more units. The expert system 100 may provide interactive, computer-implemented support services to the customer to satisfy the expert assistance required or desired by the customer.

The expert system 100 may be utilized by a requester 150 through an associated device 160. The requester 150 may be the customer of the one or more units or any other individual or group assisting or associated with the one or more units. For example, the requester 150 may be a technician and a customer, together troubleshooting a problem, seeking guidance related to a performance issue, and/or inquiring about additional training. The expert system 100 may be accessed by accessing a website specified for the expert system 100. Other access mechanisms are possible.

To initiate the support services provided by the expert system 100, a query is generated and provided to the system 100. The query may be related to at least one aspect associated with the one or more units. The query may be a problem statement, performance issue, or training request provided by the requester 150. For example, in a web-based expert system 100, the requester 150 may have an option to create a statement related to the query. With such an option, the expert system 100 may limit the query to a pre-defined number of words and/or provide other constraints related to the query. Alternatively, the requester 150 may be presented with questions to identify the query for which support services are requested. Another option for providing the query is for the requester 150 to provide one or a few key terms related to the query. Based upon the key terms, the expert system 100 may then generate and provide to the requester 150 a set of questions, the answers to which may identify and/or specify the query. Yet another option for providing the query to the expert system 100 is for the requester 150 to indicate the one or more units for which support services are sought. The expert system 100 may then provide a diagram or illustration of the one or more units, with a request for the requester 150 to select an element or component of the one or more units. Such selection may serve as the query.

The query component 120 may operate to receive the query created by the requester 150. The query component 120 may include a first communication module 125 that receives the query over the network 170. The first communication module 125 may serve as a link between the device 160 of the user 150 and the expert system 100.

The answer component 130 may function to identify one or more possible answers to the query. The query may be communicated between the query component 120 and the answer component 130. The answer component 130 may consult the database 110 and/or the knowledge base 115 to aid in the identification of the answers to the query. The knowledge base 115 may provide resources to the answer component 130 for identifying the one or more possible answers. For example, the knowledge base 115 may include rules, trees, and logic related to the one or more units and thus the query related to at least one aspect of the one or more units. The answer component may obtain the associated information related to the query from the knowledge base 115 and may process the information to provide one or more answers to the query to the requester 150.

The answer component 130 may also use key terms of the query to search the database 110 and/or the knowledge base 115. For example, key terms may be linked with a set of questions for the requester 150 and/or with a set of possible answers. The answer component 130 may obtain the questions and/or answers from the database 110 and/or the knowledge base 115 and may provide the questions and/or answers to the requester 150. Alternatively or additionally, the answer component 130 may consult, via the network 170, an external database 180 that is made available to the expert system 100. An expert may be consulted to identify the one or more possible answers to the query. For example, the administrator 140 or another individual or group with knowledge of the one or more units related to the query may be directly consulted, through the network 170.

The answer component 130 may further function to provide the one or more possible answers to the requester 150. This may be facilitated over the network 170 by a second communication module 135. The first and second communication modules 125 and 135 may be separate or individual modules. The one or more possible answers, as well as the query and other related information, may be accessible to the requester 150 through a display of the device 160. Additionally, the administrator 140 may utilize the administrator device 145 to view any query and associated information.

The query component 120 may further identify supplemental information related to the query. The supplemental information may assist the requester 150 by providing context to the query or may simply provide knowledge that may be useful during the operation of the unit and/or units. The supplemental information may be provided by the expert system 100 from the answer component 130, may be provided from resources of the knowledge base 115, and may be displayed on a display of the requester device 160. Further, the database 110 may store the supplemental information with the query for future use or reference. The supplemental information may include, but is not limited to, spreadsheets, operational information, operational specifications, training material, drawings, photographs, and/or animations, each related to an aspect of the query.

Another feature of the expert system 100 may include an interactive question and answer session between the requester 150 and the system 100. After generating and providing the query to the expert system 100, the requester 150 may be prompted to provide information related to the query. The information may be necessary to more accurately determine the query and the context of the query. The information requested by the expert system 100 may include operating conditions, data or measurements to be collected by the requester 150, and/or further detail related to the query. The query component 120 may provide the prompts and may receive the information from the requester. With the information and the original query, the answer component 130 may identify the one or more possible answers to the query.

The prompt to the requester 150 for information related to the query may include one or more questions related to the query. The information provided by the requester 150 may include responses to each question in the form of yes, no, or uncertain, for example. An uncertain response may indicate that an answer is unavailable, that there is no answer to the question, or that the requester 150 does not know the answer to the question. The answers to the questions may be utilized by the answer component 130 in identifying the one or more possible answers to the query. For an uncertain response provided by the requester 150, the answer component 130 may identify at least two possible answers to the query. This ensures that a possible answer is not eliminated.

The answer component 130 may consult an interactive decision tree in using the information to identify the one or more possible answers. The interactive decision tree may be a graphical representation of at least a portion of the knowledge base 115 related to the unit or units, and the graphical representation may includes branches containing multiple answers to each question related to the query. The answer component 130 may further provide the interactive decision tree to the requester 150. The interactive decision tree may aid the requester 150 in the interactive session with the expert system 100. Additionally, the interactive decision tree may serve as a learning or training tool for the requester 150. The requester 150 may utilize the interactive decision tree to advance in the interactive question-answer process. For example, the requester 150, by examining the tree, may realize that certain answers within the tree are known and may advance further in the tree to a more relevant question.

Upon identification of the one or more answers to the query, the answer component 130 may rank the one or more answers and provide them to the requester 150 in the ranked order. The answers may be ranked according to a confidence level in which a higher ranked answer is more likely to provide a more efficient and/or reasonable solution, as determined by the expert system 100. Other ranking criteria may instead be used. In addition to the answers, further operational or supplemental information may be included to the requester. The expert system 100 may also provide the requester with an offer to directly speak with or otherwise communicate with an expert with knowledge related to the query and the unit and/or units.

FIGS. 2-7 are exemplary screen shots of the use of an exemplary expert system 100 for interactive, computer-implemented support services related to at least one aspect of a unit or units. The expert system 100 may be provided by an outside source to create a framework, shell, and user interface of the expert system 100. For example, an outside source may create the windows, scroll bars, and boxes illustrated in the exemplary screen shots of FIGS. 2-7. The content of the windows and boxes, for example, may then be populated by the knowledge base 115, the database 110, and the external database 180. In one example, the framework of the expert system 100 is Corvid software created by Exsys Inc. Other frameworks may also be used.

Figure 2:
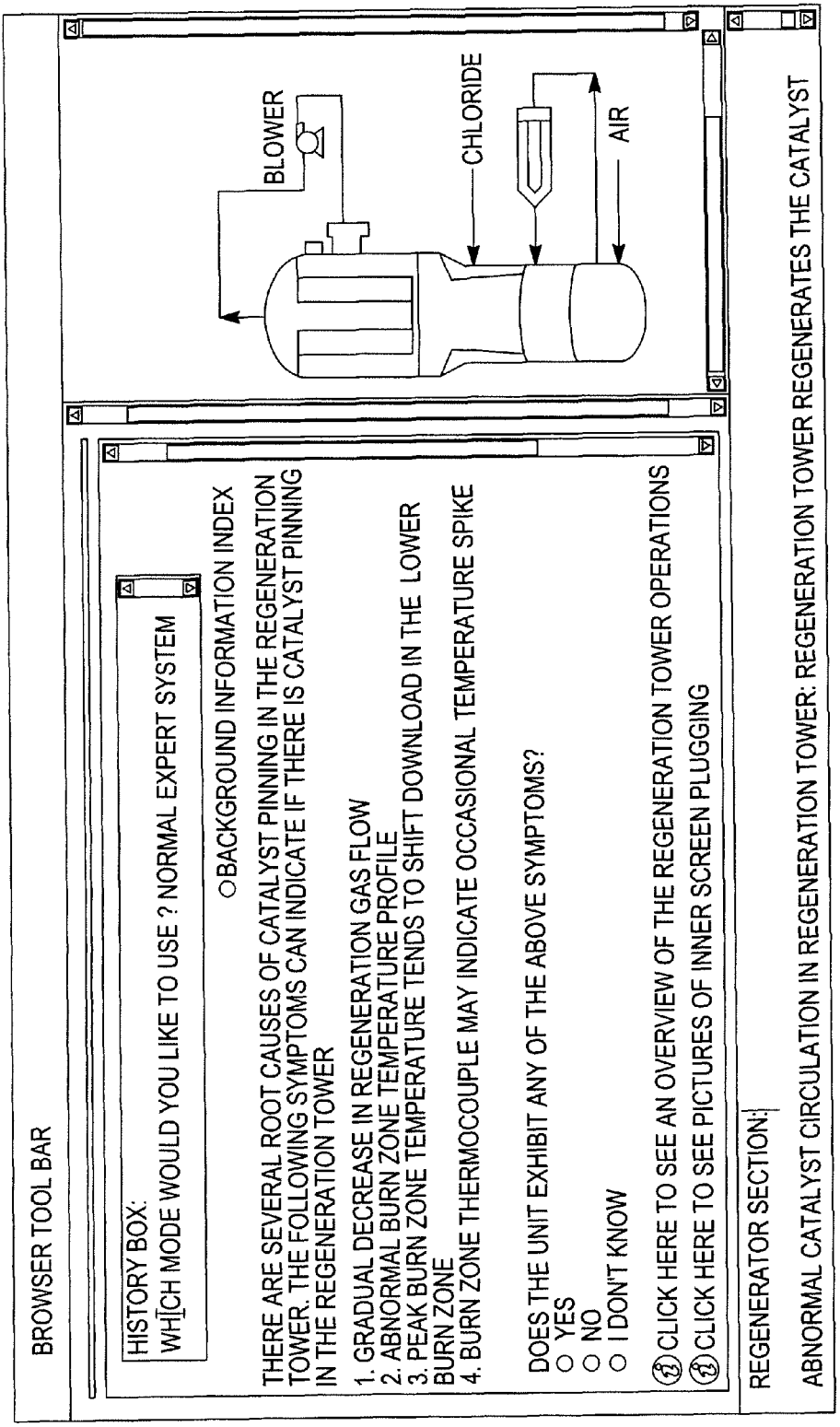
FIGS. 2-7 are exemplary screen shots of the use of an exemplary expert system for interactive, computer-implemented support services.

In FIG. 2, an example of a question provided to the requester 150 utilizing the expert system 100 is shown. The question may be generated by the answer component 130, which obtained the question from resources of the knowledge base 125 or from information stored in the databases 110 and 180. The requester 150 is presented with three answer choices and an opportunity to view operational information and informative pictures. A history box is also included, indicating previous questions and answers.

Figure 3:
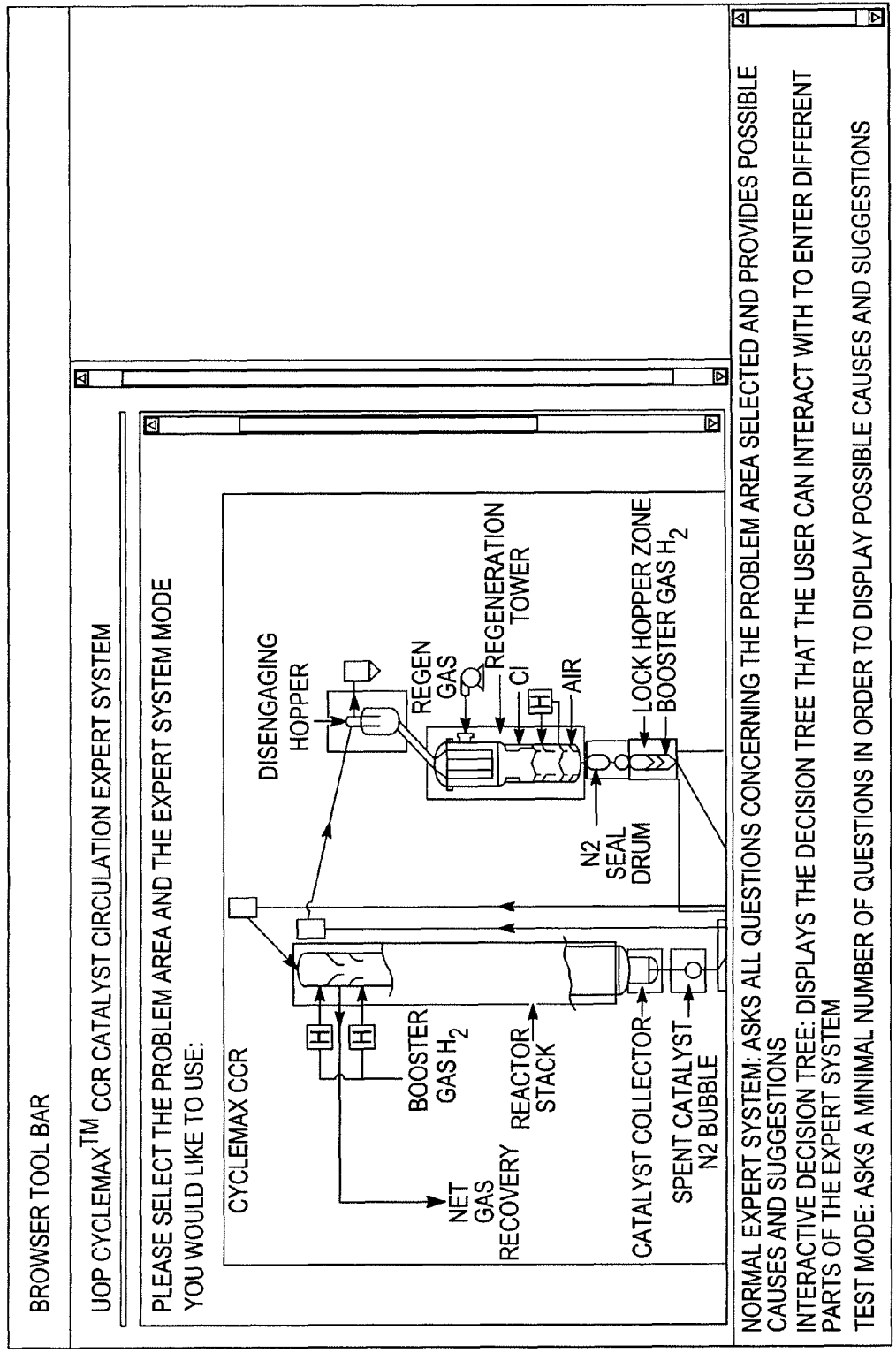

FIG. 3 is an exemplary screen shot showing an option to indicate an area of the unit and/or units with which the requester is experiencing problems. This option may be used to specify or more clearly indicate the query to the expert system 100. Or this option may be used as part of the interactive question and answer session between the requester 150 and the expert system 100.

Figure 4:
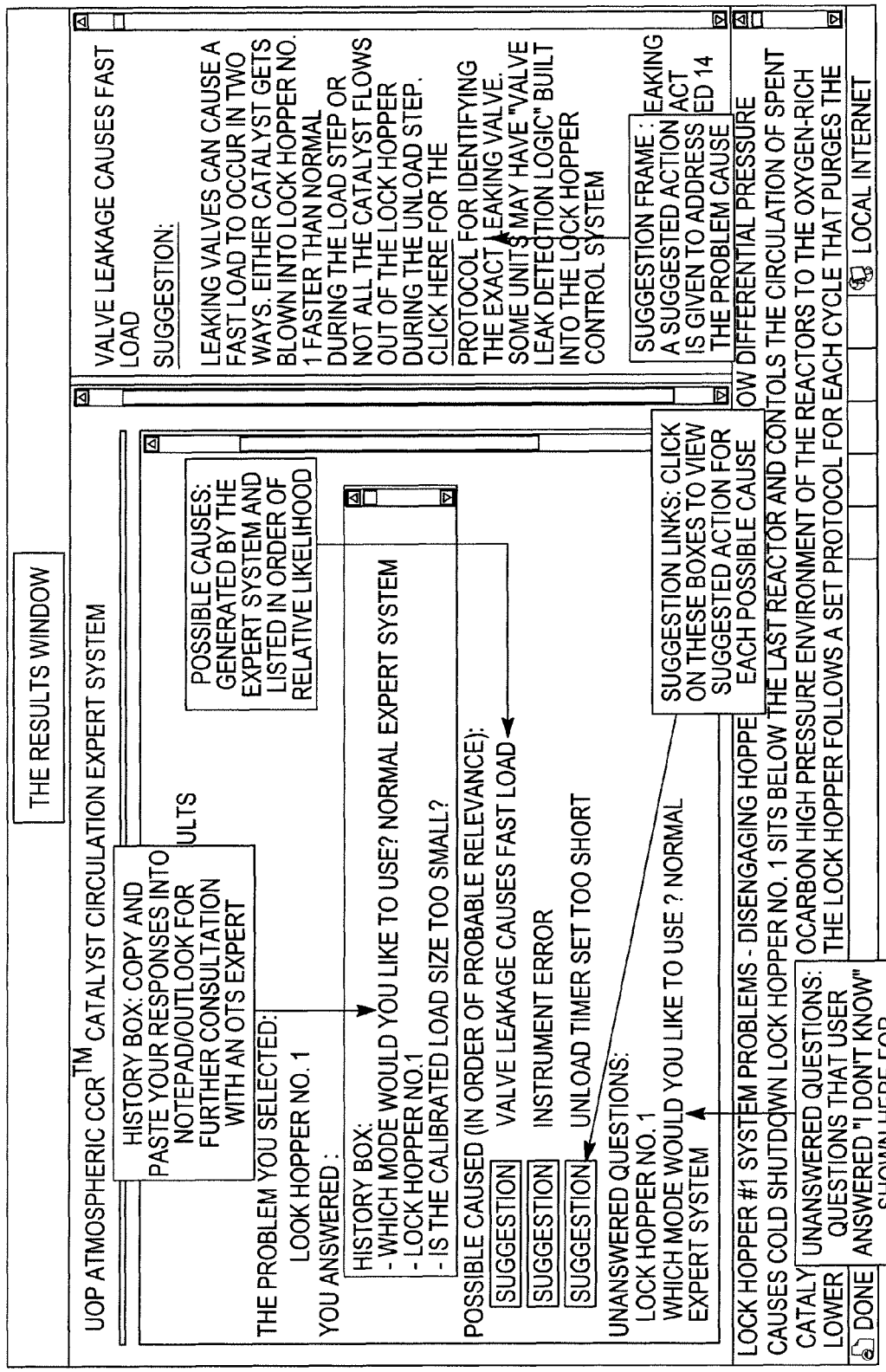

FIG. 4 is an additional exemplary screen shot of the operation of the expert system 100. In this screen shot, a results page is shown where the one or more answers to the query is provided to the requester 150. A history box is again included, detailing the questions and answers from the support services session. Two suggestions are provided, each with a confidence level. Further detail related to the suggestions are provided in a suggestion frame. Unanswered questions are also provided within the results window.

Figure 5:
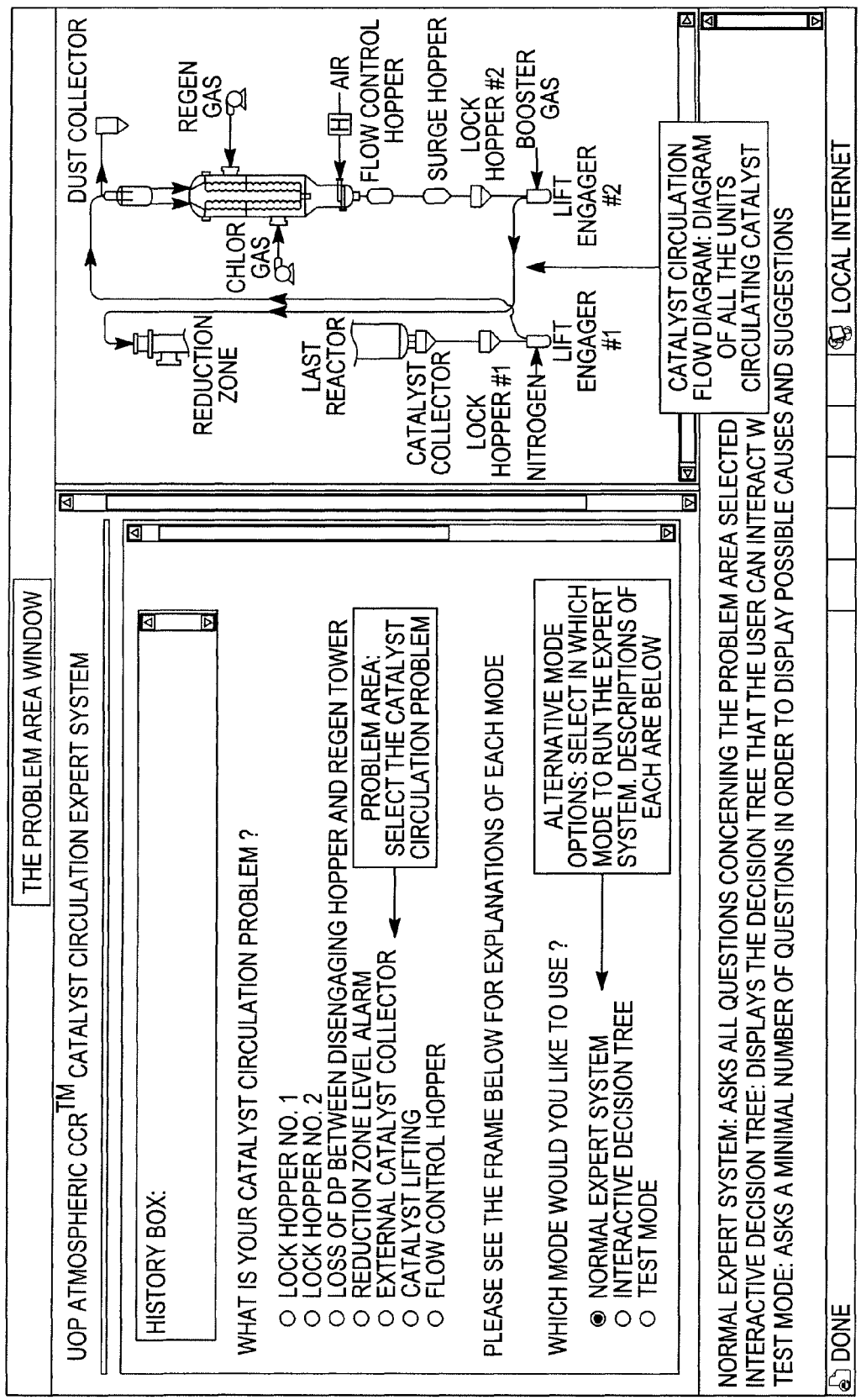
Figure 6:
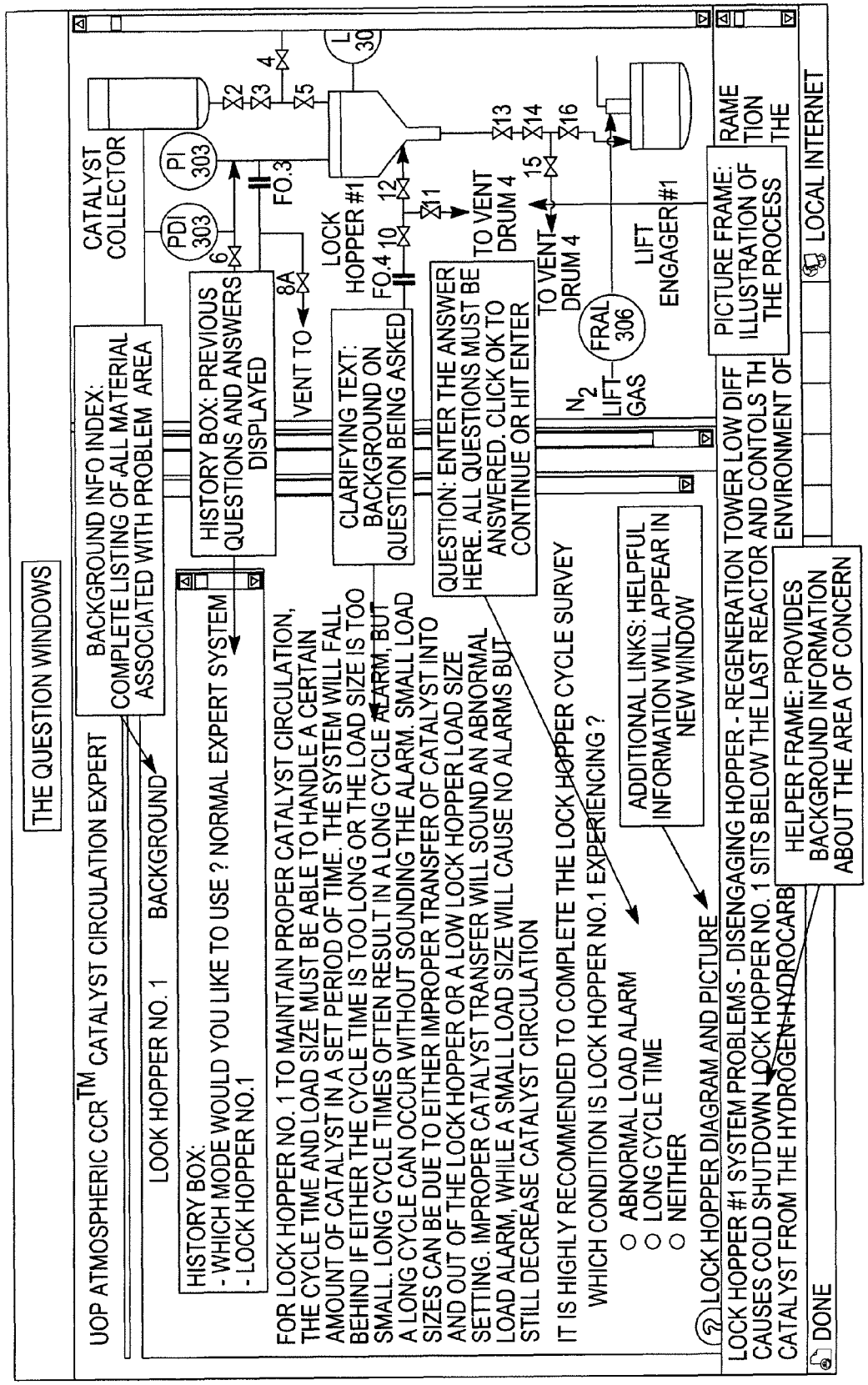

In FIG. 5, a problem area window is shown, which may be initially used for the requester 150 to indicate the query related to the one or more units. A question may initially be presented in which various problem areas are identified. The initial page may also provide an opportunity to select a mode of operation. A normal mode, an interactive decision tree mode, or a test mode may be used and selected by the requester 150. FIG. 6 is an example of a screen shot after the query has been identified. A history box displays the selections made from FIG. 5. Background information is provided that expands upon the question being asked below. A recommended activity is included for the requester 150 to perform. A question is provided to more clearly define the problem or situation experienced by the requester 150. Furthermore, links to helpful and related information, as well as a picture frame with a diagram illustrating a portion of the unit or units, are included.

Figure 7:
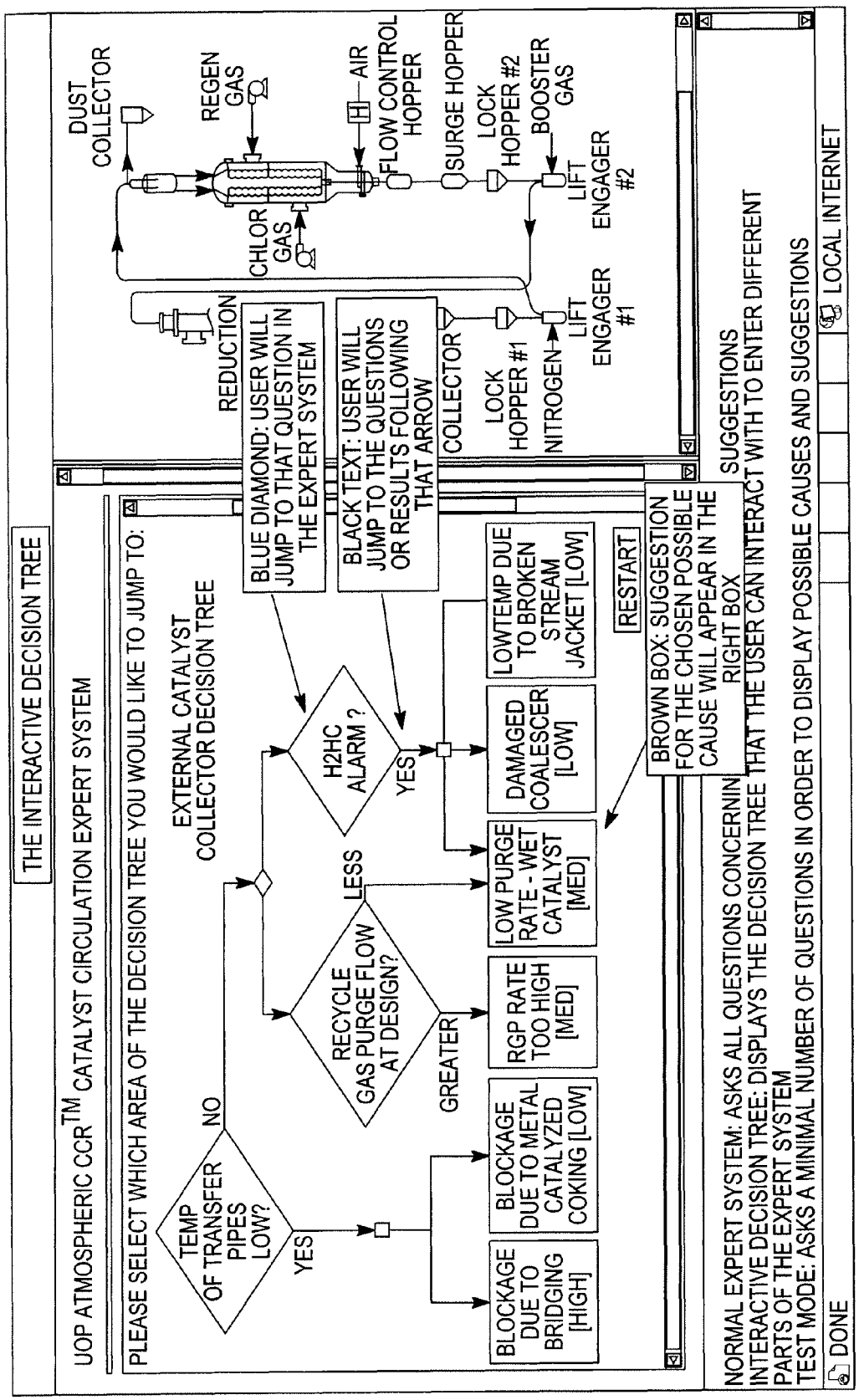

An interactive decision tree is shown in the screen shot of FIG. 7. The interactive decision tree, which may be a graphical representation of at least a portion of the knowledge base 115 related to the unit or units, may be used by the expert system 100 and provided to the requester 150. Various questions are presented in diamond-shaped boxes. The answer to each question may lead to a final answer or to a further question.

As an example of use of the expert system 100, a user is experiencing an operating problem with catalyst circulation in a CCR Platforming™ unit. He or she begins by entering the expert system 100 and is prompted to identify the problem area of interest in the problem area window (see FIGS. 3 and 5). The user is then presented with a sequence of questions and supplementary contextual information (such as FIGS. 2 and 6). By answering these questions based on the best available information, the user is led down a diagnostic path that narrows down the problem to a small number of possible causes. These are ranked in order of their relevance and are displayed in the Results Window (see FIG. 4). Each possible cause is linked with a corresponding suggested action shown on the right side of the Results Window (see FIG. 4). The user evaluates the suggested actions and either implements the suggestions as appropriate to solve the problem or uses the suggestions as the basis for further consultation with technology experts.

Figure 8:
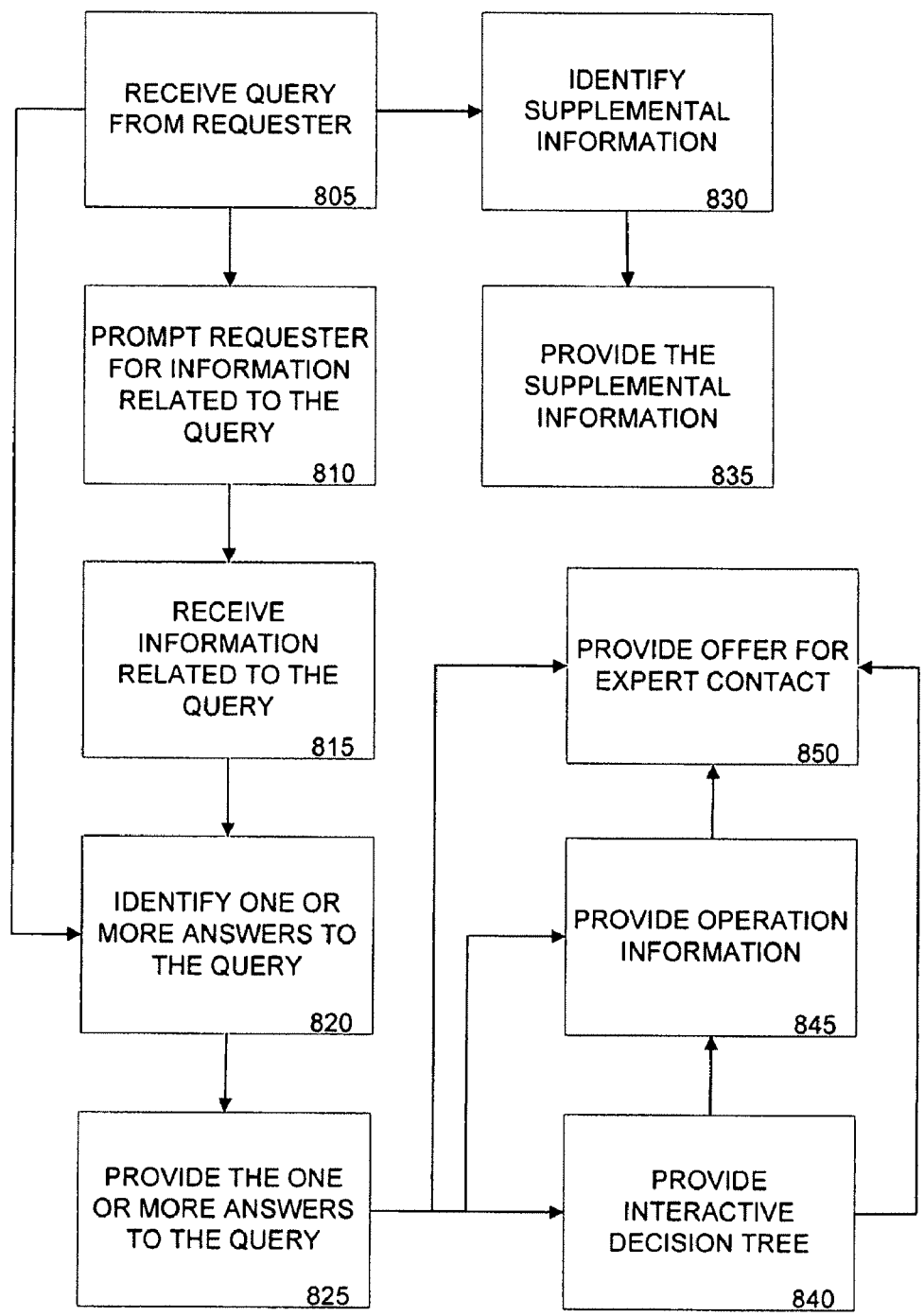
FIG. 8 is a flowchart illustrating an exemplary method of delivering support services related to a chemical processing unit or units to a customer.

FIG. 8 is a flowchart illustrating an exemplary method of delivering support services related to a chemical processing unit or units to a customer. The method may include providing interactive, computer-implemented support services to the customer during at least a portion of a lifespan of the unit or units. The support services may be provided electronically over a remotely-accessible internet website, for example. The units may be custom-designed units that interact with one another to provide one or more products. Further, the multiple of custom-designed units may each include pre-defined components, options, and functionalities that may be selected by a customer. The interactive, computer-implemented support services may be applied to any of the multiple units.

At 805, a query related to at least one aspect associated with the unit or units is received by the expert system 100 from a requester 150, which may be the customer or an individual or group working with or for the customer. The query may be a problem the requester is experiencing with the unit or units. The query may be a performance issue related to the unit or units and/or a training question related to the unit or units.

At 810, the expert system 100 may prompt the requester 150 for information related to the query. The information may be necessary or beneficial to the system 100 in determining the answers to the query. If the system 100 determines that information related to the query is necessary and/or beneficial, the prompt at 810 may occur prior to the identification of answers. At 815, the expert system 100 may receive the requested information from the requester 150.

Then, at 820, the one or more possible answers to the query is identified based upon the query and the requested information related to the query. At 825, the one or more answers to the query is provided to the requester 150.

The prompt to the requester 150 for additional information related to the query may include a presentation of questions. The receipt of the requested information may include responses to the questions in the form of yes, no, uncertain, or the like. If an uncertain answer is received, the expert system 100 may provide at least two answers to the query so as not to eliminate a possible answer.

If further information related to the query is deemed unnecessary or unbeneficial, the expert system 100 may proceed directly to 820 to operate to identify one or more possible answers to the query. Then at 825, the one or more possible answers to the query identified by the expert system 100, without the use of extra information, are provided to the requester. The one or more possible answers may be ranked based upon predefined criteria and may be provided to the requester 150 in order of the ranking.

At 830, supplemental information related to the query is identified by the expert system 100, and, at 835, the supplemental information is provided to the requester 150. The identification and delivery of the supplemental information may be performed before, during, or after the identification of answers to the query at 820 and the providing of the answers at 825. The supplemental information related to the query may include, but is not limited to, spreadsheets, operational information, operational specifications, training material, drawings, photographs, and/or animations.

An interactive decision tree, as described above, may be consulted by the expert system 100 to identify the possible answers. The interactive decision tree may be a portion of a knowledge base 115. An internal database 110, an external database 180, the knowledge base 115, an expert with knowledge of the query and/or the units, or any combination thereof may be used to assist in the identification of answers to the query.

At 840, the interactive decision tree is optionally provided to the requester 150. At 845, operational information is optionally provided to the requester 150. The operational information may be provided in an electronic format over the network 170. At 850, an optional offer for contact with an expert with knowledge related to the query and/or the unit or units is provided. The contact may be electronic communication over the network 170. Or the requester 150 may request a site visit from the expert.

Figure 9:
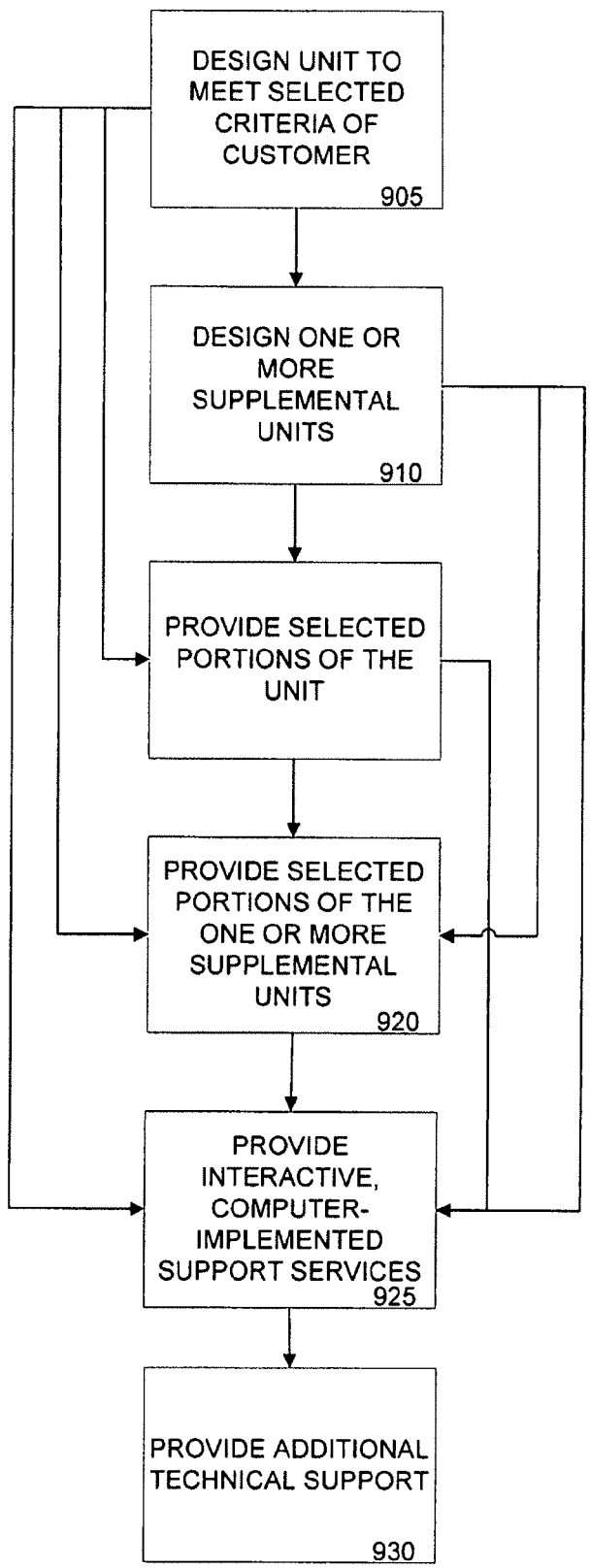
FIG. 9 is a flowchart illustrating an exemplary method of enabling a customer to provide one or more products from a unit.

FIG. 9 is a flowchart illustrating an exemplary method of enabling a customer to provide one or more products from a unit, such as a chemical processing unit. At 905, the unit is designed to meet selected criteria of the customer. The design of the unit may include one or more inter-dependent and dynamic components. The unit may further be designed to interact with one or more supplemental units. At 910, one or more of the supplemental units may be designed. The design of the unit and/or the one or more supplemental units to meet selected criteria may include customizing the unit with pre-defined, components, options, and functionalities.

At 915, selected portions of the unit are optionally provided to the customer. At 920, selected portions of the one or more supplemental units are optionally provided to the customer.

At 925, interactive, computer-implemented support services are provided to the customer. The support services may be provided during at least a portion of a lifespan of the unit and/or the one or more supplemental units. The provision of support services may include the process described with reference to FIG. 8.

At 930, technical support related to the unit and/or the supplemental units is provided. The technical support may include site visits and/or communications with one or more experts with knowledge related to the units.

Figure 10:
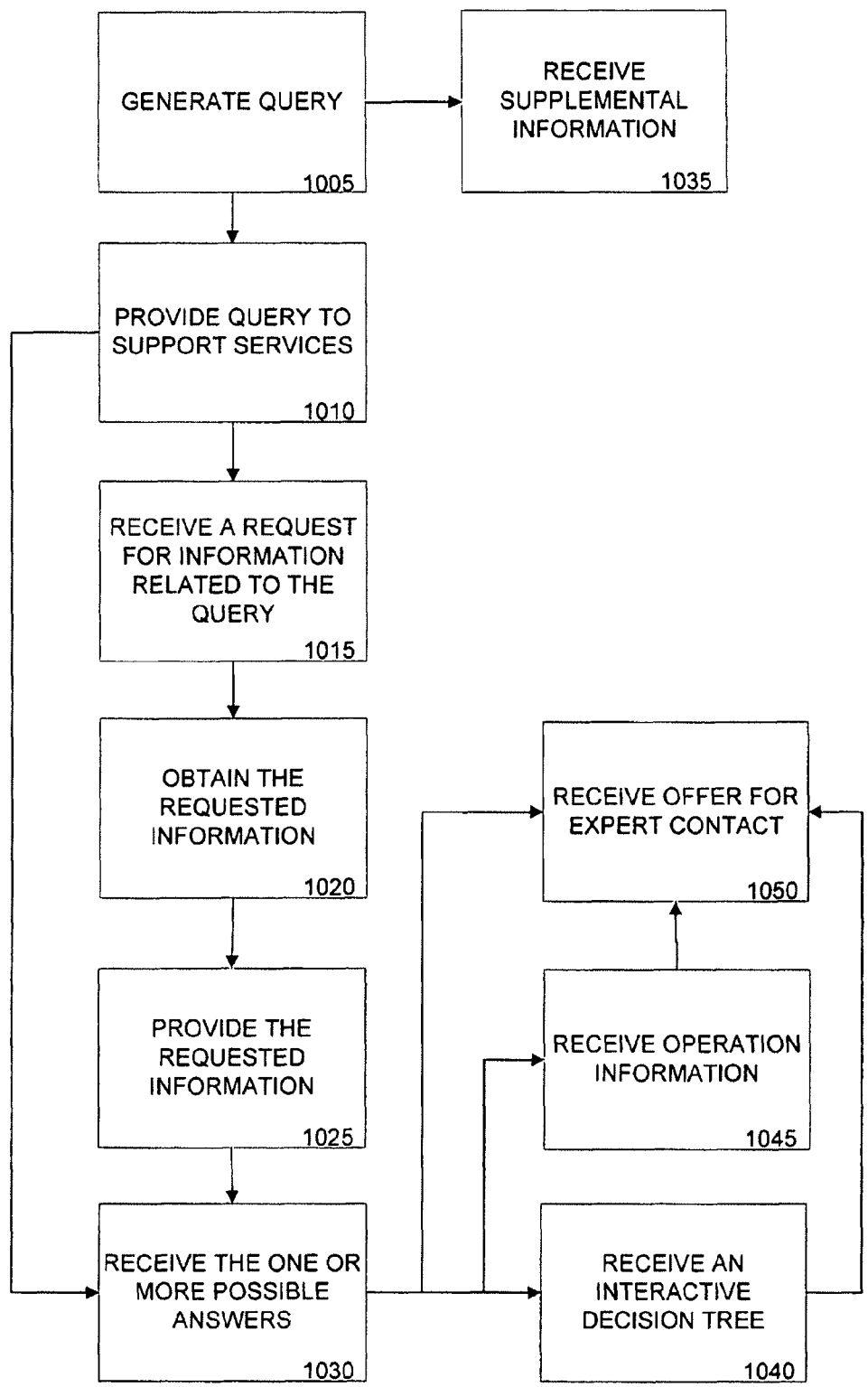
FIG. 10 is a flowchart illustrating an exemplary method of utilizing an interactive, computer-implemented support service related to a unit or units.

FIG. 10 is a flowchart illustrating an exemplary method of utilizing an interactive, computer-implemented support services related to a unit or units.

At 1005, a query related to at least one aspect associated with the unit or units is generated by a requester 150, which may be the customer or an individual or group working with or for the customer. The query may be a problem the requester 150 is experiencing with the unit or units. The query may be a performance issue related to the unit or units and/or a training question related to the unit or units. The query may be generated by selecting an option from a list containing issues related to the unit or units. Alternatively, a diagram or picture of the unit or units may be provided to the requester 150, and the requester 150 may indicate the query by selecting a portion of the unit or units from the diagram or picture.

At 1010, the query is provided by the requester 150 to the expert system 100 to receive support services related to the query and the unit or units. The query may be provided over the network 170.

At 1015, the requester 150 may optionally receive a request for information related to the query. The information may be necessary or beneficial to the expert system 100 in determining the answers to the query from the requester 150. At 1020, the requester 150 may obtain the requested information for the expert system 100. The requester 150 may need to gather data or perform tests for the information or may have the information readily available. At 1025, the requester 150 provides the information over the network 170 to the expert system 100.

At 1030, the one or more possible answers to the query, based upon the query and/or the requested information related to the query is provided to the requester 150. The one or more possible answers may be ranked based upon predefined criteria and may be provided to the requester 150 in order of the ranking.

The request received by the requester 150 for additional information related to the query may include a presentation of questions. The receipt of the requested information may include responses to the questions in the form of yes, no, or uncertain. If an uncertain answer is received, the expert system 100 may provide at least two answers to the query so as not to eliminate a possible answer.

At 1035, supplemental information related to the query may be provided by the expert system 100 to the requester 150. The delivery of the supplemental information may be performed before, during, or after the query is generated and provided to the expert system 100. The supplemental information related to the query may include, but is not limited to, spreadsheets, operational information, operational specifications, training material, drawings, photographs, and/or animations.

At 1040, an interactive decision tree is optionally received by the requester 150. An interactive decision tree, as described above, may be consulted by the expert system 100 to identify the possible answers. The interactive decision tree may be a portion of a knowledge base 115.

At 1045, operational information is optionally received by the requester 150. The operational information may be provided in an electronic format over the network 170. At 1050, an optional offer for contact with an expert with knowledge related to the query and/or the unit or units may be received by the requester 150. The contact may be electronic communication over the network 170. Or the requester 150 may request a site visit from the expert.

The expert system 100 described herein may be utilized for various types of units. The unit or units may be a chemical processing unit or units and may be all of or a portion of one or more of a petroleum refinery, a petrochemical plant, a chemicals purification plant, a natural gas processing unit, a gas separations unit, a refinery product blending unit, a bio-chemical unit, a bio-fuel unit, a fine chemicals unit, an oil and gas production unit, and a pharmaceuticals unit.

As is apparent from the above, all or portions of the various systems, methods, and aspects may be embodied in hardware, software, or a combination of both.

The foregoing examples are provided merely for the purpose of explanation and are in no way to be construed as limiting. While reference to various embodiments are shown, the words used herein are words of description and illustration, rather than words of limitation. Further, although reference to particular means, materials, and embodiments are shown, there is no limitation to the particulars disclosed herein. Rather, the embodiments extend to all functionally equivalent structures, methods, and sues, such as are within the scope of the appended claims.

The invention claimed is:

1. A method of delivering support services related to a chemical processing unit or units to a customer, wherein the chemical processing unit or units comprise a portion of at least one of a petroleum refinery, a petrochemical production plant, a chemicals purification plant, a natural gas processing unit, a gas separations unit, a refinery product blending unit, a bio-chemical production unit, a bio-fuel production unit, a fine chemicals production unit, an oil and gas production unit, and a pharmaceuticals production unit, the method comprising:

providing interactive, computer-implemented support services to the customer during at least a portion of a lifespan of the unit or units, comprising:

receiving a query related to at least one aspect associated with the unit or units from a requester;

prompting the requester for information related to the query by presenting questions related to the query;

receiving the information relating to the query from the requester by receiving responses to the questions, the responses comprising one of (i) yes; (ii) no; or (iii) uncertain;

providing a diagram or illustration of the unit or units and prompting the requestor to select an element or component of the one or more units;

receiving the selection of the element or component of the diagram or illustration;

identifying one or more possible answers to the query based upon the query, the responses to the questions, and the selection of the element or component of the diagram or illustration; and providing the one or more possible answers to the requester.

2. The method of claim 1, wherein providing interactive, computer-implemented support services to the customer comprises electronically providing support services to the customer through a remotely-accessible internet website.

3. The method of claim 1, wherein providing interactive, computer-implemented support services to the customer further comprises:

identifying supplemental information related to the query; and providing the supplemental information to the requester.

4. The method of claim 3, wherein the supplemental information related to the query comprises at least one of the group consisting of spreadsheets, operational information, operational specifications, training material, drawings, photographs, animations and combinations thereof, each related to an aspect of the query.

5. The method of claim 1, wherein identifying one or more possible answers to the requester comprises identifying, for each uncertain response, at least two possible answers to the query.

6. The method of claim 5, wherein identifying, for each uncertain response, at least two possible answers to the query comprises consulting an interactive decision tree, wherein the interactive decision tree is a graphical representation of at least a portion of a knowledge base related to the unit or units, and wherein the graphical representation includes branches containing multiple answers to each question related to the query.

7. The method of claim 1, wherein identifying one or more possible answers to the query comprises:
   consulting at least one source to obtain the one or more possible answers to the query.

8. The method of claim 7, wherein the at least one source comprises at least one of (i) at least one expert with knowledge of the query; (ii) a knowledge base; (iii) an internal database; and (iv) an external database.

9. The method of claim 1, wherein identifying one or more possible answers to the query comprises:
   consulting an interactive decision tree to identify one or more possible answers to the query based upon the query.

10. The method of claim 9, further comprising:
    providing the interactive decision tree to the requester.

11. The method of claim 1, wherein the query comprises one of (i) a problem; (ii) a performance issue related to the unit or units; and (iii) a training question related to the unit or units.

12. The method of claim 1, wherein providing one or more possible answers to the requester comprises:
    ranking the one or more possible answers based upon pre-defined criteria; and
    providing the one or more possible answers in order of the ranking.

13. The method of claim 1, wherein the method of delivering support services further comprises:
    providing operational information in an electronic format to the requester.

14. The method of claim 1, wherein the method of delivering support services further comprises:
    providing to the requester an offer for direct contact with an expert with knowledge related to the query.

15. A method of enabling a customer to provide one or more products from a chemical processing unit, wherein the chemical processing unit or units comprises a portion of at least one of a petroleum refinery, a petrochemical production plant, a chemicals purification plant, a natural gas processing unit, a gas separations unit, a refinery product blending unit, a bio-chemical production unit, a bio-fuel production unit, a fine chemicals production unit, an oil and gas production unit, and a pharmaceuticals production unit, the method comprising:
   designing the unit to meet selected criteria of the customer, to include one or more inter-dependent and dynamic components, and to interact with one or more supplemental units; and
   providing interactive, computer-implemented support services to the customer during at least a portion of a lifespan of one of the group consisting of the unit, the one or more supplemental units and combinations thereof, the support services comprising:
   receiving a query related to at least one aspect associated with one of the group consisting of the unit, the one or more supplemental units and combinations thereof from a requester;
   prompting the requester for information related to the query by presenting questions related to the query;
   receiving the information relating to the query from the requester by receiving responses to the questions, the responses comprising one of (i) yes; (ii) no; or (iii) uncertain;
   providing a diagram or illustration of the unit or units and prompting the requestor to select an element or component of the one or more units;
   receiving the selection of the element or component of the diagram or illustration;
   identifying one or more possible answers to the query based upon the query, the responses to the questions, and the selection of the element or component of the diagram or illustration; and
   providing the one or more possible answers to the requester.

16. A method of delivering support services related to a multiplicity of custom-designed chemical processing units to at least one customer, wherein the chemical processing unit or units comprise a portion of at least one of a petroleum refinery, a petrochemical production plant, a chemicals purification plant, a natural gas processing unit, a gas separations unit, a refinery product blending unit, a bio-chemical production unit, a bio-fuel production unit, a fine chemicals production unit, an oil and gas production unit, and a pharmaceuticals production unit, the method comprising:
   providing interactive, computer-implemented support services to the at least one customer during at least a portion of a lifespan of the multiplicity of custom-designed units, the interactive, computer-implemented support services adapted to be applied to any of the multiplicity of custom-designed units and comprising:
   receiving a query related to at least one aspect associated with at least one of the multiplicity of custom-designed units and receiving a selection of an element or component of the one or more units from a diagram or illustration of the unit or units, from a requester;
   identifying one or more possible answers to the query based at least in part on the selection of an element or component; and
   providing the one or more possible answers to the requester.

17. An expert system for providing interactive, computer-implemented support services to a customer, the support services being related to a chemical processing unit or units during at least a portion of a lifespan of the unit or units, wherein the chemical processing unit or units comprise a portion of at least one of a petroleum refinery, a petrochemical production plant, a chemicals purification plant, a natural gas processing unit, a gas separations unit, a refinery product blending unit, a bio-chemical production unit, a bio-fuel production unit, a fine chemicals production unit, an oil and gas production unit, and a pharmaceuticals production unit, the system comprising:
   a query component that receives a query related to at least one aspect associated with the unit or units from a requester;
   an answer component that identifies one or more possible answers to the query and that provides the one or more possible answers to the requester;
   a knowledge base that provides resources to the answer component to identify the one or more possible answers to the query;
   a database that stores the query with the possible answers; and
   a display that displays the query, a diagram or illustration of the unit or units, and the one or more possible answers.

18. A method of utilizing an interactive, computer-implemented support service related to a chemical processing unit or units, the method comprising:

generating a query related to at least one aspect associated with the unit or units during at least a portion of a lifespan of the unit or units, wherein the unit or units comprise a portion of at least one of the group consisting of a petroleum refinery, a petrochemical production plant, a chemical purification plant, a natural gas processing unit, a gas separation unit, a refinery product blending unit, a bio-chemical unit, a bio-fuel production unit, a fine chemicals production unit, an oil and gas production unit, and a pharmaceuticals production unit;

selecting an element or component of the chemical processing unit or units from a diagram or illustration of the unit or units of the interactive computer-implement support service, providing the query and the selection of an element or component of the chemical processing unit to the support service; and receiving one or more possible answers to the query.

* * * * *